United States Patent [19]

Hartman

[11] Patent Number: 4,671,891
[45] Date of Patent: Jun. 9, 1987

[54] BLEACHING COMPOSITIONS

[75] Inventor: Frederick A. Hartman, Cincinnati, Ohio

[73] Assignee: The Procter & Gamble Company, Cincinnati, Ohio

[21] Appl. No.: 830,250

[22] Filed: Feb. 18, 1986

Related U.S. Application Data

[63] Continuation of Ser. No. 532,457, Sep. 16, 1983, abandoned, which is a continuation of Ser. No. 430,565, Sep. 30, 1982, abandoned.

[51] Int. Cl.$^4$ .................. C01B 15/10; C11D 3/395
[52] U.S. Cl. .................. 252/186.42; 252/95; 252/102; 252/186.1
[58] Field of Search .................. 252/186.38, 186.39, 252/186.4, 186.42, 95, 102; 8/111, 107

[56] References Cited

U.S. PATENT DOCUMENTS

| | | | |
|---|---|---|---|
| 3,338,839 | 8/1967 | MacKellar et al. | 252/186.38 |
| 3,583,924 | 6/1971 | Demangeon | 252/186.38 X |
| 3,822,114 | 7/1974 | Montgomery | 252/186.38 X |
| 4,006,092 | 2/1977 | Jones | 252/186.38 X |
| 4,225,451 | 9/1980 | McCrudden et al. | 252/186.26 X |
| 4,283,301 | 8/1981 | Diehl | 252/186.22 X |
| 4,399,094 | 8/1983 | Gray et al. | 252/91 |
| 4,412,934 | 11/1983 | Churg et al. | 252/186.38 |
| 4,525,292 | 6/1985 | Cushman et al. | 252/186.38 X |
| 4,536,314 | 8/1985 | Hardy et al. | 252/186.26 X |
| 4,539,130 | 9/1985 | Thompson et al. | 252/186.25 X |

FOREIGN PATENT DOCUMENTS

| | | | |
|---|---|---|---|
| 0068547 | 1/1983 | European Pat. Off. | 252/186.23 |
| 1038693 | 12/1955 | Fed. Rep. of Germany | 252/186.42 |

*Primary Examiner*—John F. Terapane
*Assistant Examiner*—Virginia B. Caress
*Attorney, Agent, or Firm*—Robert B. Aylor; Richard C. Witte; Thomas H. O'Flaherty

[57] ABSTRACT

This invention relates to bleaching compositions. More particularly, this invention relates to bleaching compositions that provide effective and efficient bleaching performance on textiles. Such bleaching performance is obtained over an extremely wide class of stains and wide range of temperatures of the bleaching solution of pH. The bleaching compositions within the invention contain a halogenated peroxybenzoic acid and a bleach activator that contains a carbonyl carbon atom that can potentially react with such peroxybenzoic acid to form a diacyl peroxide compound or essentially any peroxycarboxylic acid and a bleach activator that contains a carbonyl carbon atom that has an alkyl group containing from about 5 to about 17 carbon atoms and can potentially react with a peroxycarboxylic acid to form a diacyl peroxide compound. In a highly preferred embodiment the bleaching compositions within the invention are detergent compositions.

4 Claims, No Drawings

BLEACHING COMPOSITIONS

CROSS-REFERENCE TO RELATED APPLICATIONS

This is a continuation of application Ser. No. 532,457, filed on Sept. 16, 1983, now abandoned, which is a continuation of Ser. No. 430,565 filed on Sept. 30, 1982, now abandoned.

BACKGROUND INFORMATION

This invention relates to bleaching compositions. More particularly, this invention relates to bleaching compositions that provide effective and efficient bleaching performance on textiles. Such bleaching performance is obtained over an extremely wide class of stains and wide range of temperatures of the bleaching solution, i.e., the bleach and water mixture, and pH. The bleaching compositions within the invention contain a halogenated peroxybenzoic acid and a bleach activator that contains a carbonyl carbon atom that can potentially react with such peroxybenzoic acid to form a diacyl peroxide compound or essentially any peroxycarboxylic acid and a bleach activator that contains a carbonyl carbon atom that has an alkyl group containing from about 5 to about 17 carbon atoms and can potentially react with the peroxycarboxylic acid to form a diacyl peroxide compound. In a highly preferred embodiment the bleaching compositions within the invention are detergent compositions.

It has long been known that peroxygen bleaches that yield hydrogen peroxide in an aqueous solution provide a desirable level of bleaching performance, but that they are also extremely temperature dependent. Such bleaches are essentially only practicable and/or effective in bleaching solutions wherein the solution temperature is above about 60° C. At bleach solution temperatures of about 60° C. peroxygen bleaches are only partially effective, due to their low level of reactivity. Therefore, in order to obtain a desirable level of bleaching performance extremely high levels of peroxygen bleach must be added to the system. As the bleach solution temperature is lowered below 60° C., even higher levels of peroxygen bleach must be added to the system in order to obtain a desirable level of bleaching performance. The temperature dependence of peroxygen bleaches is significant because such bleaches are commonly used as a detergent adjuvant in textile wash processes that utilize an automatic household washing machine at wash water temperatures below 60° C. Such wash temperatures are utilized because of textile care and energy considerations. As a consequence of such wash processes, there has been much industrial research to develop substances, generally referred to as bleach activators, that render peroxygen bleaches effective at bleach solution temperatures below 60° C. Numerous substances have been disclosed in the art as effective bleach activators.

Typically, the substances that have been utilized as bleach activators are substances that react with the perhydroxide anion of hydrogen peroxide, which is yielded by the peroxygen bleach in the bleaching solution, to form a peroxy acid. Peroxy acids are more reactive than the peroxygen bleach alone and, therefore, can provide bleaching at bleach solution temperatures below about 60° C. Many of the peroxy acids are peroxycarboxylic acids. The peroxycarboxylic acids are derived from bleach activators that contain a carbonyl carbon that reacts with the perhydroxide anion to form the peroxycarboxylic acid. Examples of such bleach activators are disclosed in U.S. Pat. Nos. 4,248,928, Spadini et al (Feb. 3, 1981); 4,146,573, Johnston (Nov. 21, 1978) and 4,100,095, Hutchins et al (July 11, 1978).

SUMMARY OF THE INVENTION

The present invention comprises a bleaching composition containing:

(a) a halogenated peroxybenzoic acid or salt thereof; and (b) a bleach activator having the general formula:

wherein R is selected from the group consisting of H, a linear or branched alkyl, or alkylene, group containing from 1 to about 17 carbon atoms, a cyclic alkyl, or alkylene, group containing from about 3 to about 18 carbon atoms, an aryl group, an aromatic heterocyclic group, a polyarylene group consisting of two or more annelated benzenoid rings and groups in which two or more aryl or arylene substituents are covalently attached and L is a leaving group, wherein the conjugate acid of the anion formed on L has a $pK_a$ in the range of from about 4 to about 13; or (a) a peroxycarboxylic acid or salt thereof; and (b) a bleach activator having the general formula:

wherein R is an alkyl group containing from about 5 to about 17 carbon atoms and L is as defined above;

wherein the molar ratio of each peroxycarboxyl group of (a) to each carbonyl group of (b) that can potentially generate a diacyl peroxide compound is from about 10 to about 0.05.

DETAILED DESCRIPTION OF THE INVENTION

This invention relates to bleaching compositions consisting of two essential components: a halogenated (fluorinated, chlorinated, or brominated) peroxybenzoic acid and a bleach activator that contains a carbonyl carbon atom that can potentially react with such peroxybenzoic acid to form a diacyl peroxide compound or a peroxycarboxylic acid and a bleach activator that contains a carbonyl carbon atom that has an alkyl group containing from about 5 to about 17 carbon atoms and can potentially react with the peroxycarboxylic acid to form a diacyl peroxide compound, all of which are defined hereinafter. The bleaching compositions provide very effective and efficient removal and/or decoloration of stains on textiles. Also, the compositions are effective for providing dingy soil removal. Dingy soils are soils that build up on textiles after numerous cycles of usage and washing and, thus, result in a white textile having a gray tint. These soils tend to be a blend of body lipids and proteinaceous debris. The removal of this type of soil is sometimes referred to as "dingy fabric clean up". Furthermore, such bleaching performance is obtained with minimal damage to the textiles and with bleach solution temperatures as low as about 5° C. Bleaching compositions consisting only of a peroxycarboxylic acid or a peroxygen bleach capable of yielding hydrogen peroxide in an aqueous solution plus a bleach activator within the compositions of the invention, which form a peroxycarboxylic acid in the bleaching solution, are also able to provide bleaching at temperatures below about 60° C., i.e., the temperature wherein peroxygen bleaches are essentially ineffective; however, they provide neither the effectiveness nor the efficiency of the bleaching compositions within the invention.

The bleaching compositions within the invention are extremely effective. Such compositions provide a superior level of bleaching performance over a very wide class of stains. Bleaching compositions consisting of only a peroxycarboxylic acid or a peroxygen bleach capable of yielding hydrogen peroxide in an aqueous solution plus a bleach activator within the compositions of the invention, which form a peroxycarboxylic acid in the bleaching solution, do not provide the superior level of bleaching performance over a very wide class of stains. Such compositions provide, at best, a superior level of bleaching performance for only a narrow class of stains. Such performance is obtained primarily on beverage type stains, e.g., tea and wine. This severely limits the practicability of such compositions because there are numerous other types of common stains. Without being bound by theory, it is believed that this stain specificity is based upon the chemical structure of the stain. Beverage type stains consist essentially of aromatic type compounds. Other common stains, such as grass, ink and tomato, have structures which are very olefinic. This structural difference is believed to be the cause of the stain specificity of such bleaching compositions. Surprisingly, only the compositions within the invention provide the superior level of bleaching performance over a very wide class of stains.

The bleaching compositions within the invention are very efficient. Extremely small quantities of such compositions provide the superior level of bleaching performance. Without being bound by theory, it is believed that the peroxycarboxylic acid reacts with the bleach activator to form a diacyl peroxide compound. Since the diacyl peroxide compound contains an —O—O— group it contains a reactive oxygen atom, generally referred to as an "active oxygen" atom. The active oxygen is the active bleaching component which reacts with and, thereby, modifies stains and/or soils on textiles. The diacyl peroxide compound is more reactive toward a wide class of stains than its corresponding peroxycarboxylic acid. This enables one to obtain the superior level of bleaching performance with very small amounts of the bleaching compositions within the invention.

Another major advantage of the bleaching compositions within the invention is that they provide the superior bleaching performance over a very wide range of pH's of the bleaching solution. Therefore, for example, when the bleaching compositions are detergent compositions one can adjust the pH of the bleaching solution so as to optimize detergency performance without sacrificing bleaching performance. Typical activated bleaching compositions, i.e., those consisting only of a peroxygen bleach capable of yielding hydrogen peroxide in an aqueous solution and a bleach activator which react in the bleaching solution to form a peroxy acid, are very pH dependent. It is believed that such pH dependence is due to that the active oxygen of the peroxy acid reacts with stains and/or soils via the formation of a dimer by the peroxy acid with its anion. Thus, in order to maximize the amount of the dimer formed it is essential that the $pK_a$ of the peroxy acid be similar to the pH of the bleaching solution. This ensures that there will be similar levels of the peroxy acid and its anion present in the bleaching solution and, therefore maximizes the amount of dimer formed. Otherwise, there will be an excess of peroxy acid as compared to its anion or vice versa; either of such excess is not utilized and, thus, as indicated by experimental evidence, bleaching performance declines. It is theorized that the bleaching compositions within the invention do not operate via the formation of a reactive dimer and, therefore, as indicated by experimental evidence, provide the superior level of bleaching performance over a wide range of pH's.

The initial pH of the bleaching solution containing the bleaching compositions within the invention is from about 6 to about 12, preferably from about 7 to about 11 and most preferably from about 8.0 to about 10.

In the compositions within the invention the ratio of the peroxycarboxylic acid to bleach activator is such that the molar ratio of each peroxycarboxyl group of the peroxycarboxylic acid to each carbonyl group of the bleach activator that can potentially generate a diacyl peroxide compound is from about 10 to about 0.05, preferably from about 1 to about 0.3 and most preferably from about 1 to about 0.7. Molar ratios of such components of from about 1 to about 0.7 are most preferred because vast excesses of either component will result in such excess not interaction with the other component and, therefore, will not provide the superior level of bleaching performance that is obtained by such components that interact with each other. It should be noted that the ratio is found to vary considerably as a function of pH. For example, if the initial pH of the bleaching solution is greater than 10, then excess bleach activator would be preferred to compensate for the amount lost due to alkaline hydrolysis of the activator.

The level of peroxycarboxylic acid within compositions of the invention is from about 0.1% to about 80%, preferably from about 5% to about 60% and most preferably from about 30% to about 60%. When the bleaching compositions within the invention are also detergent compositions it is preferred that the level of peroxycarboxylic acid is from about 0.1% to about 10% and more preferably from about 1% to about 3%.

The level of bleach activator within the compositions of the invention is from about 0.1% to about 70%, preferably from about 5% to about 70% and most preferably from about 40% to about 70%. When the bleaching compositions within the invention are also detergent compsitions it is preferred that the level of bleach activator is from about 0.1% to about 10% and more preferably from about 1% to about 3%.

The following is a detailed description of the essential and the optional components of the bleaching compositions within the invention. All percentages, parts or ratios are by weight unless otherwise indicated.

BLEACHING COMPOSITIONS COMPRISING ESSENTIALLY ANY PEROXYCABOXYLIC ACID

Essentially any peroxycarboxylic acid or salt thereof is suitable for use herein with a bleach activator that has a carbonyl carbon atom that has an alkyl group containing from about 5 to about 17 carbon atoms and can potentially react with the peroxycarboxylic acid to form a diacyl peroxide compound. Albeit some peroxycarboxylic acids are more preferred than others, it is believed that the effectiveness and efficiency of bleaching performance of essentially any peroxycarboxylic acid will be enhanced by utilizing it with such bleach activators.

The preferred peroxycarboxylic acids and salts thereof have the general formula:

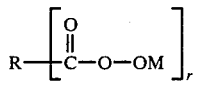

wherein R is selected from the group consisting of H, a linear or branched alkyl, or alkylene, group containing from 1 to about 18 carbon atoms, a cyclic alkyl, or alkylene, group containing from about 3 to about 18 carbon atoms, an aryl group, an aromatic heterocyclic group, a polyarylene group consisting of two or more annelated benzenoid rings and groups in which two or more aryl or arylene sustituents are covalently attached, M is H or a cation which provides water-solubility or dispersibility to the peroxycarboxylic acid and r is from 1 to the total number of hydrogen atoms on R. Preferably, M is H or an alkali metal or an alkaline earth metal, with H, magnesium, sodium and potassium being the most preferred. R can be substituted with essentially any group or groups, including an alkyl group when R is aryl or an aryl group when R is alkyl, so long as they do not interfere with the function of the peroxycarboxylic acid. The preferred alkyl, or alkylene, group substituents are $-SO_3^-M^+$ and $-COOM$ and the preferred aryl or arylene substituents are selected from the group consisting of halogens (fluorine, chlorine, or bromine), $-NO_2$, $-OCH_3$ and $-COOM$ wherein M is as defined above. Suitable aromatic heterocyclic groups include furan, thiophene and pyridine. Examples of polyarylene groups consisting of two or more annelated benzenoid rings are the naphthyl, phenanthryl and anthracenyl moieties.

The more preferred peroxycarboxylic acids and salts thereof have the general formula:

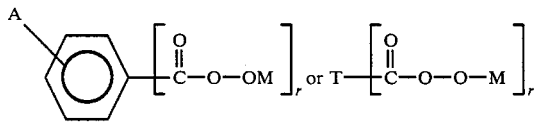

wherein A is selected from the group consisting of halogens (chlorine, fluorine, or bromine), $-NO_2$, and $-COOH$, M is as defined above, T is an alkyl group containing from about 5 to about 18 carbon atoms and r is 1 or 2.

The most preferred peroxycarboxylic acids and salts thereof have the general formula:

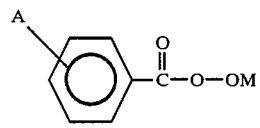

wherein A is a halogen (fluorine or chlorine), preferably Cl, and M is H or magnesium.

The bleach activators that can be utilized with essentially any peroxycarboxylic acid have the general formula:

wherein R is an alkyl group containing from about 5 to about 17 carbon atoms and L is a leaving group, wherein the conjugate acid of the anion formed on L has a $pK_a$ in the range of from about 4 to about 13.

L can be essentially any suitable leaving group. A leaving group is any group that is displaced from the bleach activator as a consequence of the nucleophilic attack on the bleach activator by the anion of the peroxycaboxylic acid. Leaving groups that exhibit such behavior are those in which their conjugate acid has a $pK_a$ in the range of from about 4 to about 13.

Preferred bleach activators are those of the above general formula wherein R is as defined in the above general formula and L is selected from the group consisting of:

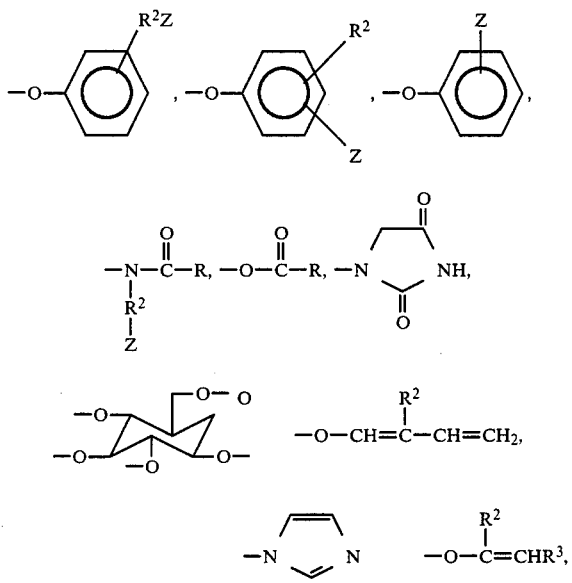

wherein R is as defined, $R^2$ is an alkyl chain containing from about 1 to about 8 carbon atoms, $R^3$ is H or $R^2$, and Z is H or a solubilizing group. The preferred solubilizing groups are $-SO_3^-M^+$, $-COO^-M^+$, $-SO_4^-M^+$, $(-N^+R_3^4)X^-$ and $O(\leftarrow NR_2^4$ and most preferably $-SO_3^-M^+$ and $-COO^-M^+$ wherein $R^4$ is an alkyl chain containing from about 1 to about 4 carbon atoms, M is a cation which provides solubility to the bleach activator and X is a compatible anion. Preferably, M is sodium or potassium, most preferably sodium and X is a halide (fluroride, chloride, or bromide), hydroxide, methylsulfate or acetate anion. It should be noted that bleach activators with a leaving group that does not contain a solubilizing group should be well dispersed in the bleaching solution in order to assist in their dissolution.

The preferred bleach activators are those of the above general formula wherein R is a linear alkyl group containing about eight carbon atoms and L is as defined directly above.

The most preferred bleach activators have the general formula:

wherein R is an alkyl group containing from about 5 to about 17, preferably from 6 to about 11 and most preferably about 7 carbon atoms.

BLEACHING COMPOSITIONS COMPRISING A HALOGENATED PEROXYBENZOIC ACID

Essentially any halogenated peroxybenzoic acid or salt thereof can be utilized with essentially any bleach activator that contains a carbonyl carbon atom that can potentially react with such peroxybenzoic acid to form a diacyl peroxide compound, defined hereinafter. The preferred halogenated peroxybenzoic acids and salts thereof have the general formula:

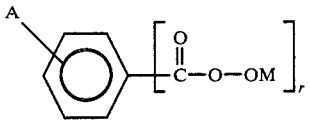

wherein A is a halogen (fluorine, chlorine, or bromine), preferably Cl; M is H or a cation which provides water-solubility or dispersability to the peroxycarboxylic acid, preferably H or an alkali metal or an alkaline earth metal and most preferably H or magnesium; r is 1 or 2 and preferably 1.

The bleach activators within the compositions of the invention that can be utilized with the halogenated (fluorinated, chlorinated, or brominated) peroxybenzoic acid have the general formula:

wherein R is selected from the group consisting of H, a linear or branched alkyl, or alkylene, group containing from 1 to about 17 carbon atoms, a cyclic alkyl, or alkylene, group containing from about 3 to about 18 carbon atoms, an aryl group, an aromatic heterocyclic group, a polyarylene group consisting of two or more annelated benzenoid rings and groups in which two or more aryl or arylene substituents are covalently attached and L is a leaving group, wherein the conjugate acid of the anion formed on L has a p$K_a$ in the range of from about 4 to about 13.

L can be essentially any suitable leaving group. A leaving group is any group that is displaced from the bleach activator as a consequence of the nucleophilic attack on the bleach activator by the anion of the peroxycarboxylic acid. Leaving groups that exhibit such behavior are those in which their conjugate acid has a p$K_a$ in the range of from about 4 to about 13.

Preferred bleach activators are those of the above general formula wherein R is as defined in the above general formula and L is selected from the group consisting of:

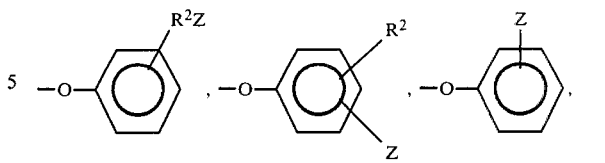

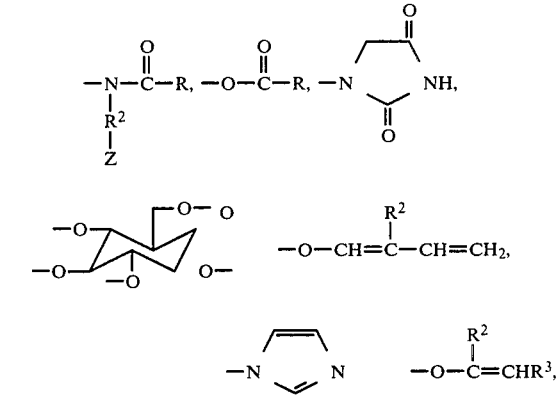

wherein R is as defined, $R^2$ is an alkyl chain containing from about 1 to about 8 carbon atoms, $R^3$ is H or $R^2$, and Z is H or a solubilizing group. The preferred solubilizing groups are $-SO_3^-M^+$, $-COO^-M^+$, $-SO_4^-M^+$, $(-N^+R_3^4)X^-$ and $O \leftarrow NR_2^4$ and most preferably $-SO_3^-M^+$ and $-COO^-M^+$ wherein $R^4$ is an alkyl chain containing from about 1 to about 4 carbon atoms, M is a cation which provides solubility to the bleach activator and X is a compatible anion. Preferably, M is sodium or potassium, most preferably sodium and X is a halide (fluoride, chloride, or bromide), hydroxide, methylsulfate or acetate anion. It should be noted that the bleach activators with a leaving group that does not contain a solubilizing group should be well dispersed in the bleaching solution in order to assist in their dissolution. Also, it should be noted that L can be covalently attached to R to form a ring structure.

Even more preferred are bleach activators of the above general formula wherein L is as defined directly above and R is selected from the group consisting of an alkyl group containing from 1 to about 11 carbon atoms,

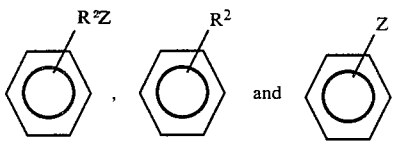

wherein $R^2$ and Z are as defined above.

The most preferred bleach activators are selected from the group consisting of:

wherein R is an alkyl group containing about 1 or about 7 carbon atoms and benzoic anhydride. These bleach activators in combination with a halogenated peroxybenzoic acid provide extremely effective and efficient bleaching performance.

OPTIONAL COMPONENTS

As a preferred embodiment, the bleaching compositions of the invention can be detergent compositions. Thus, the bleaching compositions can contain typical detergent composition components such as detergency surfactants and detergency builders. In such preferred embodiments the bleaching compositions are particularly effective. The bleaching compositions of this invention can contain all of the usual components of detergent compositions including the ingredients set forth in U.S. Pat. No. 3,936,537, Baskerville et al, incorporated herein by reference. Such components include color speckles, suds boosters, suds suppressors, antitarnish and/or anticorrosion agents, soil-suspending agents, soil-release agents, dyes, fillers, optical brighteners, germicides, alkalinity sources, hydrotropes, antioxidants, enzymes, enzyme stabilizing agents, perfumes, etc.

The detergent surfactants can be any one or more surface active agents selected from anionic, nonionic, zwitterionic, amphoteric and cationic classes and compatible mixtures thereof. Detergent surfactants useful herein are listed in U.S. Pat. No. 3,664,961, Norris, issued May 23, 1972, and in U.S. Pat. No. 3,919,678, Laughlin et al, issued Dec. 30, 1975, both incorporated herein by reference. Useful cationic surfactants also include those described in U.S. Pat. No. 4,222,905, Cockrell, issued Sept. 16, 1980, and in U.S. Pat. No. 4,239,659, Murphy, issued Dec. 16, 1980, both incorporated herein by reference. The following are representative examples of detergent surfactants useful in the present compositions.

Water-soluble salts of the higher fatty acids, i.e., "soaps", are useful anionic surfactants in the compositions herein. This includes alkali metal soaps such as the sodium, potassium, ammonium, and alkylammonium salts of higher fatty acids containing from about 8 to about 24 carbon atoms, and preferably from about 12 to about 18 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Useful anionic surfactants also include the water-soluble salts, preferably the alkali metal, ammonium and alkylammonium salts, of organic sulfuric reaction products having in their molecular structure an alkyl group containing from about 10 to about 20 carbon atoms and a sulfonic acid or sulfuric acid ester group. (Included in term "alkyl" is the alkyl portion of acyl groups.) Examples of this group of synthetic surfactants are the sodium and potassium alkyl sulfates, especially those obtained by sulfating the higher alcohols ($C_8$–$C_{18}$ carbon atoms) such as those produced by reducing the glycerides of tallow or coconut oil; and the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average numbrer of carbon atoms in the alkyl group is from about 11 to 13, abbreviated as $C_{11-13}LAS$.

Other anionic surfactants herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

Other useful anionic surfactants herein include the water-soluble salts of esters of alpha-sulfonated fatty acids containing from about 6 to 20 carbon atoms in the fatty acid group and from about 1 to 10 carbon atoms in the ester group; water-soluble salts of 2-acyloxyalkane-1-sulfonic acids containing from about 2 to 9 carbon atoms in the acyl group and from about 9 to about 23 carbon atoms in the alkane moiety; water-soluble salts of olefin and paraffin sulfonates containing from about 12 to 20 carbon atoms; and beta-alkyloxy alkane sulfonates containing from about 1 to 3 carbon atoms in the alkyl group and from about 8 to 20 carbon atoms in the alkane moiety.

Water-soluble nonionic surfactants are also useful in the compositions of the invention. Such nonionic materials include compounds produced by the condensation of alkyl, or alkylene, oxide groups (hydrophilic in nature) with an organic hydrophobic compound, which may be aliphatic or alkyl aromatic in nature. The length of the polyoxyalkylene group which is condensed with any particular hydrophobic group can be readily adjusted to yield a water-soluble compound having the desired degree of balance between hydrophilic and hydrophobic elements.

Suitable nonionic surfactants include the polyethylene oxide condensates of alkyl phenols, e.g., the condensation products of alkyl phenols having an alkyl group containing from about 6 to 15 carbon atoms, in either a straight chain or branched chain configuration, with from about 3 to 12 moles of ethylene oxide per mole of alkyl phenol.

Preferred nonionics are the water-soluble and water-dispersible condensation products of aliphatic alcohols containing from 8 to 22 carbon atoms, in either straight chain or branched configuration, with from 2 to 12 moles of ethylene oxide per mole of alcohol. Particularly preferred are the condensation products of alcohols having an alkyl group containing from about 9 to 15 carbon atoms with from about 4 to 8 moles of ethylene oxide per mole of alcohol.

Semi-polar nonionic surfactants include water-soluble amine oxides containing one alkyl moiety of from about 10 to 18 carbon atoms and two moieties selected from the group of alkyl and hydroxyalkyl moieties of from about 1 to about 3 carbon atoms; water-soluble phosphine oxides containing one alkyl moiety of about 10 to 18 carbon atoms and two moieties selected from the group consisting of alkyl groups and hydroxyalkyl groups containing from about 1 to 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Ampholytic surfactants include derivatives of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants include derivatives of aliphatic, quaternary, ammonium, phosphonium, and sulfonium compounds in which one of the aliphatic substituents contains from about 8 to 18 carbon atoms.

The level of detergent surfactant that can be employed is from 0% to about 50%, preferably from about 1% to about 30% and most preferably from about 10% to about 25% by weight of the total composition.

In addition to detergent surfactants, detergency builders can be employed in the bleaching compositions. Water-soluble inorganic or organic electrolytes are suitable builders. The builder can also be water-insoluble calcium ion exchange materials; nonlimiting examples of suitable water-soluble, inorganic detergent builders include: alkali metal carbonates, borates, phosphates, bicarbonates and silicates. Specific examples of such salts include sodium and potassium tetraborates, bicarbonates, carbonates, orthophosphates, pyrophosphates, tripolyphosphates and metaphosphates.

Examples of suitable organic alkaline detergency builders include: (1) water-soluble amino carboxylates and aminopolyacetates, for example, nitrilotriacetates, glycinates, ethylenediamine tetraacetates, N-(2-hydroxyethyl)nitrilo diacetates and diethylenetriamine pentaacetates; (2) water-soluble salts of phytic acid, for example, sodium and potassium phytates; (3) water-soluble polyphosphates, including sodium potassium, and lithium salts of ethane-1-hydroxy-1, 1-diphosphonic acid; sodium, potassium, and lithium salts of ethylene diphosphonic acid; and the like; (4) water-soluble polycarboxylates such as the salts of lactic acid, succinic acid, malonic acid, maleic acid, citric acid, carboxymethyloxysuccinic acid, 2-oxo-1,1,3-propane tricarboxylic acid, 1,1,2,2-ethane tetracarboxylic acid, mellitic acid and pyromellitic acid; (5) water-soluble polyacetals as disclosed in U.S. Pat. Nos. 4,144,266 and 4,246,495 incorporated herein by reference and (6) water-soluble polyacrylates.

Another type of detergency builder material useful in the present compositions comprises a water-soluble material capable of forming a water-insoluble reaction product with water hardness cations preferably in combination with a crystallization seed which is capable of providing growth sites for said reaction product. Such "seeded builder" compositions are fully disclosed in British Patent Specification No. 1,424,406.

A further class of detergency builder materials useful in the present invention are insoluble sodium aluminosilicates, particularly those described in U.S. Pat. No. 4,303,556 issued Dec. 1, 1981, incorporated herein by reference. This patent discloses and claims detergent compositions containing sodium aluminosilicates having the formula:

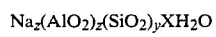

wherein z and y are integers equal to at least 6, the molar ratio of z to y is in the range of from 1.0:1 to about 0.5:1, and X is an integer from about 15 to about 264, said aluminosilicates having a calcium ion exchange capacity of at least 200 milligrams equivalent/gram and a calcium ion exchange rate of at least about 2 grains/-gallon/minute/gram. A preferred material is Zeolite A which is:

The level of detergency builder of the bleaching compositions is from 0% to about 70%, preferably from about 10% to about 60% and most preferably from about 20% to about 60%.

Buffering agents can be utilized to maintain the desired alkaline pH of the bleaching solutions. Buffering agents include, but are not limited to many of the detergency builder compounds disclosed hereinbefore. Buffering agents suitable for use herein are those well known in the detergency art.

Preferred optional ingredients include suds modifiers particularly those of suds suppressing types, exemplified by silicones, and silica-silicone mixtures. U.S. Pat. Nos. 3,933,672, issued Jan. 20, 1976 to Bartolotta et al, and 4,136,045, issued Jan. 23, 1979 to Gault et al, incorporated hereby by reference, disclose silicone suds controlling agents. Particularly useful suds suppressors are the self-emulsifying silicone suds suppressors, described in U.S. Pat. No. 4,073,118, Gault et al, issued Feb. 21, 1978, incorporated herein by reference. An example of such a compound is DB-544, commercially available from Dow Corning, which is a siloxane/glycol copolymer. Suds modifiers as described above are used at levels of up to approximately 2%, preferably from about 0.1 to about 1½% by weight of the surfactant.

Microcrystalline waxes having a melting point in the range from 35° C.-115° C. and a saponification value of less than 100 represent additional examples of preferred suds control components for use in the subject compositions, and are described in detail in U.S. Pat. No. 4,056,481, Tate, issued Nov. 1, 1977, incorporated herein by reference. The microcrystalline waxes are substantially water-insoluble, but are water-dispersible in the presence of organic surfactants. Preferred microcrystalline waxes have a melting point from about 65° C. to 100° C., a molecular weight in the range from 400–1,000; and a penetration value of at least 6, measured at 77° F. by ASTM-D1321. Suitable examples of the above waxes include: microcrystalline and oxidized microcrystalline petroleum waxes; Fischer-Tropsch and oxidized Fischer-Tropsch waxes; ozokerite; ceresin; montan wax; beeswax; candelilla; and carnauba wax.

Alkyl phosphate esters represent an additional preferred suds control agent for use herein. These preferred phosphate esters are predominantly monostearyl phosphate which, in addition thereto, can contain di- and tristearyl phosphates and monooleyl phosphate, which can contain di- and trioleyl phosphate.

Other suds control agents useful in the practice of the invention are the soap or the soap and nonionic mixtures as disclosed in U.S. Pat. Nos. 2,954,347 and 2,954,348, incorporated herein by reference.

Fluorescent or optical brighteners can be utilized within the bleaching compositions of the invention. Surprisingly, such brighteners exhibit acceptable compatibility with such compositions. Suitable anionic brighteners are disclosed in U.S. Pat. Nos. 3,537,993 Coward et al (Nov. 3, 1970) and 3,953,380 Sundby (Apr. 27, 1976), incorporated herein by reference. Nonionic brighteners can also be utilized within the compositions of the invention.

The following example is given to illustrate the parameters of and compositions within the invention. All percentages, parts and ratios are by weight unless otherwise indicated.

EXAMPLE

The following granular detergent composition was prepared:

| | % |
|---|---|
| Sodium $C_{16-18}$ alkyl sulfate | 5.5 |
| Sodium $C_{12}$ linear alkylbenzene sulfonate | 3.5 |
| $C_{14-16}$ alkyl polyethoxylate$_{2.25}$ | 5.5 |
| Sodium tripolyphosphate | 24.4 |
| Zeolite A | 17.6 |
| Sodium carbonate | 10.5 |
| Sodium silicate (2.0r) | 1.9 |
| Sodium sulfate | 21.0 |
| Water | 8.9 |
| Miscellaneous | 1.2 |

Two sets of six 5"×5" swatches consisting of five polycotton swatches each stained with one of the following stains—chili, RAGU spaghetti sauce, mustard, ink and tea—and one denim swatch stained with grass were prepared.

A laundry load consisting of one set of the six swatches, four clean terry cloth towels and one terry cloth towel soiled with 1.5 grams of a mixture of artificial body soil and vacuum cleaner soil was placed in a mini-wash system. This laundry load was then washed with 8.5 grams of the above granular detergent composition in 5.5 liters of water. This mini-wash system with such a load and granular detergent concentration simulates a conventional automatic wash process. The wash water temperature was 37° C. and the wash water contained 8 grains/gallon water hardness.

After drying, each of the swatches was visually graded by comparing it to its unwashed counterpart. A grading scale of 0 to 5 was used, with 0 indicating no stain removal and 5 indicating 100% stain removal. Each swatch was graded by three graders and then the average grade for each swatch was calculated. This average was then scale from 0 to 100, with 100 being 100% stain removal. Also, the mean for the set of swatches was calculated.

The entire procedure was repeated numerous times, but each time a different bleaching system was added to the mini-wash system one minute after the start of the wash process.

The results were as follows:

| Bleaching System | initial pH of Wash Water | % Stain Removal | | | | | | |
|---|---|---|---|---|---|---|---|---|
| | | Chili | Spaghetti | Mustard | Ink | Tea | Grass | Mean |
| 1. None | 9.7 | 62 | 60 | 64 | 61 | 62 | 58 | 61 |
| 2. m-chloroperoxybenzoic acid (3)[i] | 9.7 | 60 | 50 | 63 | 60 | 77 | 67 | 63 |
| 3. p-chloroperoxybenzoic acid (3) | 9.7 | 63 | 53 | 63 | 60 | 80 | 50 | 62 |
| 4. p-nitroperoxybenzoic acid (3) | 9.7 | 63 | 57 | 63 | 57 | 83 | 60 | 64 |
| 5. m-chloroperoxybenzoic acid (3) + 4-sulfophenyl-octanoate, sodium salt (3)[ii] | 10.1 | 83 | 87 | 73 | 77 | 63 | 73 | 76 |
| 6. m-chloroperoxybenzoic acid (3) + 4-sulfophenylacetate, sodium salt (3) | 10.0 | 87 | 90 | 60 | 77 | 70 | 77 | 77 |
| 7. p-fluoroperoxybenzoic acid | 10.0 | 73 | 60 | 50 | 57 | 73 | 60 | 63 |
| 8. p-fluoroperoxybenzoic acid (3) + 4-sulfophenyloctanoate, sodium salt (3)[ii] | 10.2 | 83 | 97 | 63 | 77 | 73 | 77 | 78 |
| 9. p-fluoroperoxybenzoic acid (3) + 4-sulfophenylactetate, sodium salt (3) | 10.0 | 87 | 77 | 57 | 77 | 73 | 60 | 72 |
| 10. Magnesium monoperoxyphthalate (6) | 10.1 | 63 | 57 | 60* | 57 | 67 | 57 | 60 |
| 11. Magnesium monoperoxyphthalate (6) + 4-sulfophenyloctanoate, sodium salt (6)[ii] | 10.8 | 97 | 90 | 100* | 63 | 70 | 73 | 83 |
| 12 Diperoxydodecanedioic acid (3) | 10.2 | 57 | 57 | 57 | 60 | 60 | 60 | 59 |
| 13. Diperoxydodecanedioic acid (3) + 4-sulfophenyl-octanoate, sodium salt (3) | 10.2 | 63 | 67 | 57 | 67 | 67 | 70 | 65 |
| 14. Peroxyhexanoic acid (3) | 9.8 | 47 | 67 | 60 | 60 | 70 | 67 | 62 |
| 15. Peroxyhexanoic acid (3) + 4-sulfophenyloctanoate, sodium salt (3) | 9.8 | 87 | 77 | 60 | 67 | 67 | 73 | 72 |
| 16. Peroxyhexanoic acid (3) + 4-sulfophenylacetate, sodium salt (3) | $^3$10 | 77 | 50 | 67 | 63 | 60 | 60 | 63 |
| 17. Peroxyhexanoic acid (3) + succinic anhydride (3) | $^3$10 | 70 | 57 | 57 | 57 | 67 | 67 | 63 |
| 18. p-chloroperoxybenzoic acid (3) + succinic | 9.5 | 90 | 77 | 53 | 70 | 80 | 73 | 74 |

-continued

| Bleaching System | initial pH of Wash Water | % Stain Removal ||||||
|---|---|---|---|---|---|---|---|
| | | Chili | Spaghetti | Mustard | Ink | Tea | Grass | Mean |
| anhydride (3) | | | | | | | | |
| 19. m-chloroperoxybenzoic acid (3) + benzoic anhydride (4.5) | [3]10 | 90 | 97 | 80 | 77 | 67 | 83 | 82 |

[i]indicates the parts per million of active oxygen available in the wash water from m-chloroperoxybenzoic acid. This same denotation is utilized in all the examples.
[ii]indicates the potential parts per million of active oxygen in the wash water available as a diacyl peroxide compound.
*This swatch consisted of T-shirt material.

Bleaching systems 5, 6, 8, 9, 11, 13, 15, 18 and 19 which are within the compositions of the invention, provided significantly more stain removal than bleaching systems 2-4, 7, 10, 12, 14, 16, and 17 which are outside the compositions of the invention. Bleaching systems 2-4, 7 and 10 did not contain bleach activator within the compositions of the invention. Bleaching system 16 and 17 did not contain a peroxycarboxylic acid and bleach activator combination which is within the compositions of the invention.

What is claimed is:

1. A bleaching composition comprising:
   (a) from about 0.1% to about 80% of a peroxycarboxylic acid or salt thereof having the general formula:

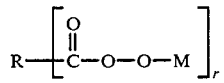

wherein R is selected from the group consisting of H, a linear or branched alkyl, or alkylene group, containing from 1 to about 18 carbon atoms, a cyclic alkyl, or alkylene, group containing from about 3 to about 18 carbon atoms, an aryl group, an aromatic heterocyclic group, and mixtures thereof, M is H or a cation which provides water solubility or dispersibility to the peroxycarboxylic acid and r is from 1 to the total number of replaceable hydrogen atoms on R; and
   (b) from about 0.1% to about 70% of a bleach activator having the general formula:

wherein R is an alkyl group containing from 5 to about 17 carbon atoms and L is a leaving group, wherein the conjugate acid of the anion formed on L has a pK$_a$ in the range of from about 4 to about 13; and L is selected from the group consisting of:

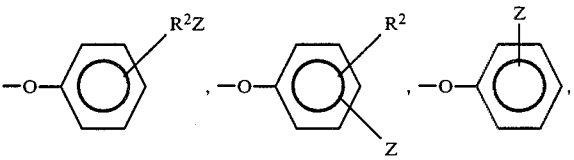

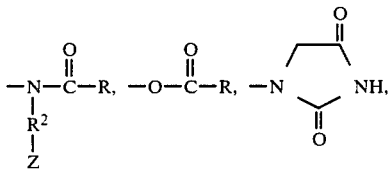

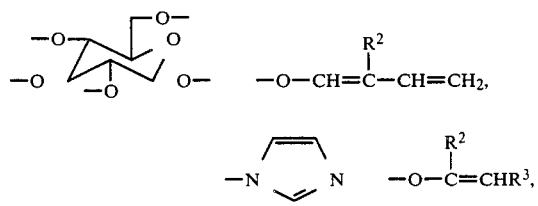

and mixtures thereof; wherein R is an alkyl group containing from 5 to about 17 carbon atoms and wherein R$^2$ is an alkyl chain containing from about 1 to about 8 carbon atoms, R$^3$ is H or R$^2$, and Z is H or a solubilizing group.

2. A composition according to claim 1 wherein each R in the bleach activator contains from about 6 to about 11 carbon atoms.

3. A composition according to claim 2 where the initial pH of a bleaching solution containing the bleaching composition is from about 8 to about 10.

4. A composition according to claim 2 wherein there is from about 0.1% to about 10% of (a) and from about 0.1% to about 10% of (b).

* * * * *